United States Patent [19]

Sonoi et al.

[11] Patent Number: 5,672,758

[45] Date of Patent: Sep. 30, 1997

[54] BISAMINOTHIOPHENOL COMPOUND, PROCESS FOR PRODUCING THE SAME AND CURING AGENT FOR FLUORINE-CONTAINING ELASTOMER COMPRISING THE SAME

[75] Inventors: Takehiro Sonoi; Haruyoshi Tatsu, both of Ibaraki, Japan; Lev Solomonovich German, deceased, late of Moscow, Russian Federation, by Elena N. German, executrix; Valerii Romanovich Polishchuk, deceased, late of Lod, Israel, by Margarita Polischuk, executrix

[73] Assignee: Nippon Mektron, Limited, Tokyo, Japan

[21] Appl. No.: 550,870

[22] Filed: Oct. 31, 1995

[30] Foreign Application Priority Data

Nov. 17, 1994 [JP] Japan .................................. 6-308199

[51] Int. Cl.$^6$ .................................................. C07C 323/34
[52] U.S. Cl. .................. 564/440; 564/327; 252/182.15; 548/156
[58] Field of Search .................. 564/327, 440; 252/182.15

[56] References Cited

U.S. PATENT DOCUMENTS 5,223,599  6/1993  Gajewski .......................... 528/59

FOREIGN PATENT DOCUMENTS 0 606 883 A1  1/1994  European Pat. Off. .
705873  4/1996  European Pat. Off. .

OTHER PUBLICATIONS

Comptes Rendus Hebdomadaires Des Seances De L'academie Des Sciences, A Bouanne et al., Chimie Macromoleculaire, vol. 279, No. 5. 1974, pp. 187–190.
Chemical Abstracts, vol. 117, No. 12, 1992. Columbus, Ohio, US; abstract No. 113668b, *abstract*.

Primary Examiner—Robert Gerstl
Attorney, Agent, or Firm—Barnes & Thornburg

[57] ABSTRACT

2,2-bis(4-aminophenyl)hexafluoropropane is allowed to react with potassium thiocyanate and bromine to obtain 2,2-bis (5-amino-4,6-benzothiazolyl)hexafluoropropane, which is allowed to further react successively with potassium hydroxide and hydrochloric acid to obtain 2,2-bis(4-amino-3-mercaptophenyl)hexafluoropropane, which is a novel compound applicable as a curing agent for a fluorine-containing elastomer having CN groups as cross-linkable groups.

5 Claims, No Drawings

BISAMINOTHIOPHENOL COMPOUND, PROCESS FOR PRODUCING THE SAME AND CURING AGENT FOR FLUORINE-CONTAINING ELASTOMER COMPRISING THE SAME

BACKGROUND OF THE INVENTION

1. FIELD OF THE INVENTION

The present invention relates to a bisaminothiophenol compound, and more particularly to a bisaminothiophenol compound effectively applicable as a curing agent for a fluorine-containing elastomer having nitrile group as cross-linkable group.

2. RELATED ART

The following bisaminothiophenol compounds are known and are used as starting materials for polybenzothiazole compounds as heat-resistant resin, etc.

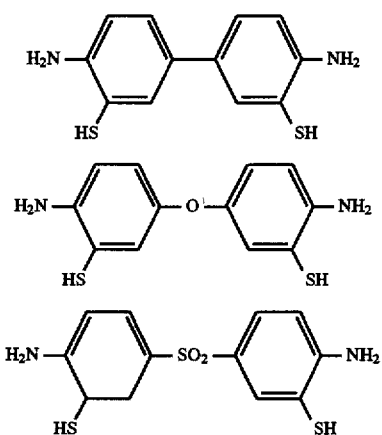

SUMMARY OF THE INVENTION

An object of the present invention is to provide a novel bisaminothiophenol compound, which can be effectively applied as a curing agent for fluorine-containing elastomer having nitrile group as cross-linkable group.

According to the present invention, there is provided a novel bisaminothiophenol compound represented by the following general formula [I]:

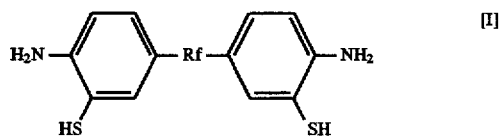

wherein Rf is a perfluoroalkylidene group of $C_1$ to $C_{10}$, which can take a salt form, such as hydrochloride, hydrobromide, sulfate, borate, carboxylate, etc.

DETAILED DESCRIPTION OF THE INVENTION

The present bisaminothiophenol compound can be produced according to a well known synthesis process through a series of the following steps:

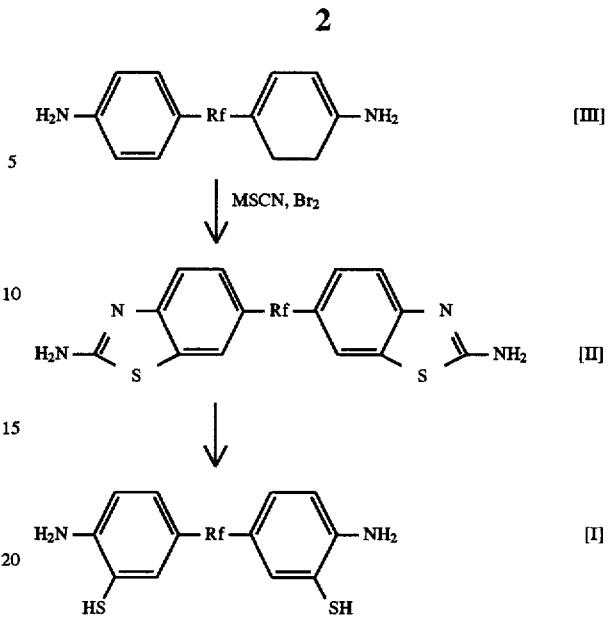

Reaction of [III]→[II]:

A solution of bromine in glacial acetic acid is dropwise added to a solution of a bisaminophenyl compound [III] and an alkali metal thiocyanate such as potassium thiocyanate or sodium thiocyanate in excess of an equimolar amount to that of bisaminophenyl compound [III] in glacial acetic acid at room temperature with stirring and then water is added thereto. The mixture is heated up to the boiling point and then cooled and filtered. Sodium hydrogen carbonate is added to the filtrate to obtain a bisaminobenzothiazole compound [II] as precipitates. It seems that bromine acts as an oxidizing agent to make the thiocyanate addition reaction with the aromatic nucleus, followed by a nucleophilic ring-closing reaction between the thiocyano group and the amine group.

Generally, 2,2-bis(4-aminophenyl)hexafluoropropane can be used as the bisaminophenyl compound [III]. Besides, 1,2-bis(4-aminophenyl)tetrafluoroethane, etc. can be used.

Reaction of [II]→[I]:

The thus obtained bisaminobenzothiazole compound [II] is added to an aqueous solution of an alkali metal hydroxide such as potassium hydroxide or sodium hydroxide in an inert gas atomosphere at a temperature of about 110° to about 130° C., and then the mixture is slowly heated to about 260° C. to conduct reaction until generation of ammonia is ceased. Then, the temperature is lowered down to about 200° C. After addition of water thereto, the reaction mixture is cooled down to room temperature. Then, an aqueous dilute solution of an inorganic acid such as a concentrated hydrochloric acid is added to the reaction mixture to make pH 6, and then glacial acetic acid is added thereto to obtain a bisaminothiophenol compound [I] as precipitates.

The thus obtained bisaminothiophenol compound or its salt can be used as a curing agent for a fluorine-containing elastomer having CN group as cross-linkable group.

The fluorine-containing elastomer for use in the present invention includes a terpolymer of tetrafluoroethylene, perfluoro(lower alkyl vinyl ether) or perfluoro(lower alkoxy-lower alkyl vinyl ether) and a small amount (i.e. about 0.1 to 5% by mole on the basis of the terpolymer) of perfluoro unsaturated nitrile compound.

The perfluoro unsaturated nitrile compound includes, for example, the following compounds:

| | |
|---|---|
| CF$_2$ = CFO(CF$_2$)nOCF(CF$_3$)CN | (n: 2 ~ 5) |
| CF$_2$ = CF[OCF$_2$CF(CF$_3$)nO(CF$_2$)mCN | (n: 1 ~ 2, m: 1 ~ 4) |
| CF$_2$ = CF[OCF$_2$CF(CF$_3$)]nCN | (n: 1 ~ 5) |
| CF$_2$ = CFO(CF$_2$)nCN | (n: 1 ~ 10) |

About 0.1 to about 5 parts by weight, preferably about 1 to about 3 parts by weight, of the present bisaminothiophenol compound is added as a curing agent to 100 parts by weight of the fluorine-containing elastomer having CN group as cross-linkable group due to the incorporation of the perfluoro unsaturated nitrile compound by copolymerization. The fluorine-containing elastomer can further contain necessary additives such as a filler, a reinforcing agent, a stabilizer, a plasticizer, a lubricant, a processing aid, etc. besides the bisaminothiophenol compound. The resulting mixture is kneaded in a roll mill or the like and then subjected to a primary vulcanization (press vulcanization) at a temperature of about 160° to about 250° C. for about 30 to about 60 minutes and then to a secondary vulcanization (oven vulcanization) at a temperature of about 200° to about 300° C. for about 10 to about 50 hours, preferably in an inert gas atmosphere.

According to the present invention, a novel bisaminothiophenol compound effectively applicable as a curing agent for a fluorine-containing elastomer having CN group as cross-linkable group can be provided.

PREFERRED EMBODIMENTS OF THE INVENTION

The present invention will be described in detail below, referring to Examples.

EXAMPLE 1

A solution containing 92.8 g (0.58 moles) of bromine in 20 ml of glacial acetic acid was dropwise added to a solution containing 80 g (0.24 moles) of 2,2-bis(4-aminophenyl)hexafluoropropane and 120 g (1.24 moles) of potassium thiocyanate in 280 ml of glacial acetic acid with stirring over one hour. After the dropwise addition, the mixture was stirred for further 2 hours and left standing overnight. Then, 1 liter of water was added thereto, and the mixture was heated to the boiling point and then cooled and filtered.

Sodium hydrogen carbonate was added to the filtrate, and the resulting precipitates were recovered by filtration, washed with water and dried, whereby 102 g of desired 2,2-bis(5-amino-4,6-benzothiazolyl)hexafluoropropane was obtained (yield: 95%).

Melting point: 262°~266° C.

Elemental analysis (C$_{17}$H$_{10}$F$_6$N$_4$S$_2$): Calculated; C 45.53%, H 2.33%, F 25.45%, N 12.50%, S 14.28% Found; C 45.23%, H 2.35%, F 24.87%, N 11.74%, S 13.80%

Mass spectrum: 448(relative intensity 86)M$^+$ 379(100) [M—CF$_3$]$^+$ 310(15)[M—2CF$_3$]$^+$ $^{19}$F NMR (δ: DMSO): −15.2(s) (CF$_3$COOH base)

$^1$H NMR (δ: DMSO): H(1), H(2)=6.32 ppm(AB q.) J$_{AB}$=7.9 Hz H(3)=6.72 ppm(br. s.) H(4)=6.8 ppm(br. s.) H(1):H(2):H(3):H(4)=1:1:1:2

EXAMPLE 2

120 g (2.14 moles) of potassium hydroxide and 16 ml of water were charged into a round bottom flask and heated at 120° C. in an argon atmosphere while stirring the mixture until potassium hydroxide was dissolved into water. Then, 44.8 g (0.1 mole) of 2,2-bis(5-amino-4,6-benzothiazolyl)hexafluoropropane obtained in Example 1 was added thereto also in the argon atmosphere with stirring, and the mixture was slowly heated up to 250° C., and then stirred for further 20 minutes. Then, the mixture was heated up to 260° C. and can kept at that temperature for about 10 minutes until generation of ammonia was completely ceased to conduct the reaction. Then, the reaction temperature was lowered down to 200° C., and 600 ml of deaerated water was slowly added thereto. Then, the mixture was cooled down to 15° C. An aqueous dilute solution containing 240 ml of concentrated hydrochloric acid in 240 ml of deaerated water was added thereto to make pH 6, and then 40 ml of glacial acetic acid was slowly added thereto. The resulting precipitates were recovered by filtration, washed with water and dried, whereby 37 g of 2,2-bis(4-amino-3-mercaptophenyl)hexafluoropropane was obtained as the ultimate product (yield:93%).

Melting point: 85° C.

Elemental analysis (C$_{15}$H$_{12}$F$_6$N$_2$S$_2$): Calculated; C 45.23%, H 3.01%, F 28.64%, N 7.03%, S 16.08% Found; C 45.03%, H 2.88%, F 25.37%, N 6.79%, S 15.98%

Mass spectrum: 398M$^+$, 364[M—H$_2$S]$^+$, 329[M—CF$_3$]$^+$, 295[M—H$_2$S—CF$_3$]$^+$ $^{19}$F NMR (δ: DMSO.d$_6$): −14.55 ppm(s) (CF$_3$COOH base)

$^1$H NMR (δ): H(1), H(2)=6.05 ppm(AB q.) J$_{AB}$=9 Hz H(HS)=4.8 ppm H(H$_2$N)=6.14 ppm

EXAMPLE 3

200 ml of distilled water, 3.3 g of ammonium perfluorooctanoate and 2.3 g of KH$_2$PO$_4$ were charged into a stainless steel autoclave having a net capacity of 500 ml, and the gas inside the autoclave was replaced with a nitrogen gas. The autoclave was subjected to pressure reduction and cooled down to 0° C. Then, the following compounds were successively charged into the autoclave:

| | |
|---|---|
| Perfluoro(5-cyanopentyl vinyl ether) [CNVE] | 6 g |
| Perfluoro(methyl vinyl ether) [FMVE] | 60 g |
| Tetrafluoroethylene [TFE] | 36 g |

Then, the autoclave was heated to 60° C., and then 10 ml of an aqueous solution containing 0.15 g of sodium sulfite and 10 ml of an aqueous solution containing 1.10 g of ammonium persulfate were charged thereto to conduct polymerization reaction for 16 hours.

After the end of the reaction, unreacted gases were purged from the autoclave to recover an aqueous latex. Then, the aqueous latex was kept in a refrigerator at −30° C. for 24 hours for freezing. After defreezing, the solidified polymer was washed with 10% ethanol at 50% and dried under reduced pressure at 80° C. for 6 hours, whereby 75 g of terpolymer was obtained (yield: 74%). As a result of infrared absorption analysis CN group absorption was observed at 2266 cm$^{-1}$ and it was found that the terpolymer had a composition of 1.0 mol. % CNVE, 57 mol. % FMVE and 42 mol. % TFE.

The following components were kneaded through a double roll rubber mill and subjected to primary vulcanization at 160° C. for 30 minutes and then to secondary vulcanization at 230° C. in a nitrogen gas atmosphere for 22 hours:

| | |
|---|---|
| Terpolymer | 100 parts by weight |
| Bisaminothiophenol of Example 1 | 1 parts by weight |
| MT carbon black | 5 parts by weight |

The thus obtained vulcanization product had the following normal state properties as a result of measurements according to JIS K-6301:

| | |
|---|---|
| Hardness (JIS-A) | 72 |
| 100% modulus | 52 kg/cm² |
| Tensile strength | 148 kg/cm² |

It was found that the present bisaminothiophenol compound was useful as a curing agent for a fluorine-containing elastomer having CN group as cross-linkable group.

What is claimed is:

1. A bisaminothiophenol compound represented by the following general formula [I]:

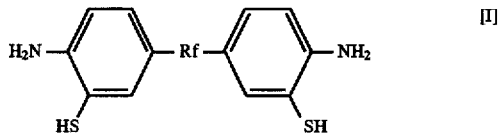

wherein Rf is a perfluoroalkylidene group having 1 to 10 carbon atoms.

2. 2,2-bis(4-amino-3-mercaptophenyl) hexafluoropropane.

3. A vulcanizing agent for a fluorine-containing elastomer having cyano group as cross-linkable groups, which comprises a bisaminothiophenol compound having the following general formula [I]:

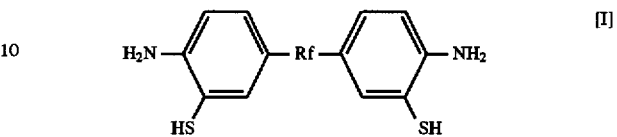

wherein Rf is a perfluoroalkylidene group having 1 to 10 carbon atoms.

4. A vulcanizing agent according to claim 3, wherein the bisaminothiophenol compound is 2,2-bis(4-amino-3-mercaptophenyl)hexafluoropropane.

5. A vulcanizing agent according to claims 3 or 4, wherein the fluorine-containing elastomer is a terpolymer comprising tetrafluoroethylene, perfluoro(lower alkyl vinyl ether) or perfluoro(lower alkoxy-lower alkyl vinyl ether) and perfluoro unsaturated nitrile compound.

* * * * *